US012698574B2

(12) United States Patent
Lee et al.

(10) Patent No.: US 12,698,574 B2
(45) Date of Patent: Aug. 4, 2026

(54) METHOD FOR SCREENING TARGET GENE USING CRISPRI SYSTEM AND USES THEREOF

(71) Applicant: CHUNGANG UNIVERSITY INDUSTRY-ACADEMIC COOPERATION FOUNDATION, Seoul (KR)

(72) Inventors: Sang Jun Lee, Gyeonggi-do (KR); Hyun Ju Kim, Gyeonggi-do (KR); Song Hee Jeong, Gyeonggi-do (KR)

(73) Assignee: CHUNGANG UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 784 days.

(21) Appl. No.: 18/146,556

(22) Filed: Dec. 27, 2022

(65) Prior Publication Data

US 2023/0295674 A1 Sep. 21, 2023

(30) Foreign Application Priority Data

Dec. 27, 2021 (KR) ........................ 10-2021-0188851
Dec. 27, 2022 (KR) ........................ 10-2022-0186232

(51) Int. Cl.
*C40B 50/06* (2006.01)
*C12N 15/10* (2006.01)

(52) U.S. Cl.
CPC .......... *C40B 50/06* (2013.01); *C12N 15/1082* (2013.01)

(58) Field of Classification Search
None
See application file for complete search history.

(56) References Cited

PUBLICATIONS

Cui et al., A CRISPRi screen in *E. coli* reveals sequence-specific toxicity of dCas9, Nature Communications, 2018.
Fang et al., Genome-scale target identification in *Escherichia coli* for high-titer production of free fatty acids, Nature Communications, 2021.
Gottl et al., CRISPRi-Library-Guided Target Identification for Engineering Carotenoid Production by Corynebacterium glutamicum, Microorganisms, 2021.
Yao et al., Pooled CRISPRi screening of the cyanobacterium *Synechocystis* sp PCC 6803 for enhanced industrial phenotypes, Nature Communications, 2020.

*Primary Examiner* — Christian C Boesen
(74) *Attorney, Agent, or Firm* — Sughrue Mion, PLLC

(57) ABSTRACT

The present invention relates to a method for screening a target gene using a clustered regularly interspaced short palindromic repeats interference (CRISPRi) system and uses thereof. According to the present disclosure, it is expected that the method may be used in wide fields as a tool for genome-scale gene function profiling and studying organisms poorly developed in genetic technology, including pathogens or industrially useful strains or cell lines, and as a platform for electronic regulatory network engineering of genes.

13 Claims, 9 Drawing Sheets
Specification includes a Sequence Listing.

D-xylose-inducible vioABCDE operon

SEQUENCE LISTING

```
Sequence total quantity: 63
SEQ ID NO: 1          moltype = DNA  length = 43
FEATURE               Location/Qualifiers
source                1..43
```

```
                         mol_type = unassigned DNA
                         organism = unidentified
SEQUENCE: 1
aaagggagtg cccaatatta gttttagagc tagaaatagc aag                      43

SEQ ID NO: 2          moltype = DNA   length = 42
FEATURE               Location/Qualifiers
source                1..42
                      mol_type = unassigned DNA
                      organism = unidentified
SEQUENCE: 2
taatattggg cactcccttt actagtatta tacctaggac tg                       42

SEQ ID NO: 3          moltype = DNA   length = 43
FEATURE               Location/Qualifiers
source                1..43
                      mol_type = unassigned DNA
                      organism = unidentified
SEQUENCE: 3
agtgggagtg cccaatatta gttttagagc tagaaatagc aag                      43

SEQ ID NO: 4          moltype = DNA   length = 39
FEATURE               Location/Qualifiers
source                1..39
                      mol_type = unassigned DNA
                      organism = unidentified
SEQUENCE: 4
taatattggg cactcccact agtattatac ctaggactg                           39

SEQ ID NO: 5          moltype = DNA   length = 43
FEATURE               Location/Qualifiers
source                1..43
                      mol_type = unassigned DNA
                      organism = unidentified
SEQUENCE: 5
actagtagtg cccaatatta gttttagagc tagaaatagc aag                      43

SEQ ID NO: 6          moltype = DNA   length = 36
FEATURE               Location/Qualifiers
source                1..36
                      mol_type = unassigned DNA
                      organism = unidentified
SEQUENCE: 6
taatattggg cactactagt attataccta ggactg                              36

SEQ ID NO: 7          moltype = DNA   length = 43
FEATURE               Location/Qualifiers
source                1..43
                      mol_type = unassigned DNA
                      organism = unidentified
SEQUENCE: 7
aatactagtg cccaatatta gttttagagc tagaaatagc aag                      43

SEQ ID NO: 8          moltype = DNA   length = 33
FEATURE               Location/Qualifiers
source                1..33
                      mol_type = unassigned DNA
                      organism = unidentified
SEQUENCE: 8
taatattggg cactagtatt atacctagga ctg                                 33

SEQ ID NO: 9          moltype = DNA   length = 43
FEATURE               Location/Qualifiers
source                1..43
                      mol_type = unassigned DNA
                      organism = unidentified
SEQUENCE: 9
taatactagt cccaatatta gttttagagc tagaaatagc aag                      43

SEQ ID NO: 10         moltype = DNA   length = 32
FEATURE               Location/Qualifiers
source                1..32
                      mol_type = unassigned DNA
                      organism = unidentified
SEQUENCE: 10
taatattggg actagtatta tacctaggac tg                                  32

SEQ ID NO: 11         moltype = DNA   length = 43
FEATURE               Location/Qualifiers
```

-continued

```
source                   1..43
                         mol_type = unassigned DNA
                         organism = unidentified
SEQUENCE: 11
ataatactag tccaatatta gttttagagc tagaaatagc aag                      43

SEQ ID NO: 12            moltype = DNA   length = 31
FEATURE                  Location/Qualifiers
source                   1..31
                         mol_type = unassigned DNA
                         organism = unidentified
SEQUENCE: 12
taatattgga ctagtattat acctaggact g                                   31

SEQ ID NO: 13            moltype = DNA   length = 43
FEATURE                  Location/Qualifiers
source                   1..43
                         mol_type = unassigned DNA
                         organism = unidentified
SEQUENCE: 13
tataatacta gtcaatatta gttttagagc tagaaatagc aag                      43

SEQ ID NO: 14            moltype = DNA   length = 30
FEATURE                  Location/Qualifiers
source                   1..30
                         mol_type = unassigned DNA
                         organism = unidentified
SEQUENCE: 14
taatattgac tagtattata cctaggactg                                     30

SEQ ID NO: 15            moltype = DNA   length = 43
FEATURE                  Location/Qualifiers
source                   1..43
                         mol_type = unassigned DNA
                         organism = unidentified
SEQUENCE: 15
gtataatact agtaatatta gttttagagc tagaaatagc aag                      43

SEQ ID NO: 16            moltype = DNA   length = 29
FEATURE                  Location/Qualifiers
source                   1..29
                         mol_type = unassigned DNA
                         organism = unidentified
SEQUENCE: 16
taatattact agtattatac ctaggactg                                      29

SEQ ID NO: 17            moltype = DNA   length = 30
FEATURE                  Location/Qualifiers
source                   1..30
                         mol_type = unassigned DNA
                         organism = unidentified
SEQUENCE: 17
gatactgggc cggcaggcgc tccattgccc                                     30

SEQ ID NO: 18            moltype = DNA   length = 30
FEATURE                  Location/Qualifiers
source                   1..30
                         mol_type = unassigned DNA
                         organism = unidentified
SEQUENCE: 18
gcaatggagc gcctgccggc ccagtatcag                                     30

SEQ ID NO: 19            moltype = DNA   length = 26
FEATURE                  Location/Qualifiers
source                   1..26
                         mol_type = unassigned DNA
                         organism = unidentified
SEQUENCE: 19
gggaaacgcc tggtatcttt atagtc                                         26

SEQ ID NO: 20            moltype = DNA   length = 41
FEATURE                  Location/Qualifiers
source                   1..41
                         mol_type = unassigned DNA
                         organism = unidentified
SEQUENCE: 20
nnnnnnnnnn nnnnnnnnnn gttttagagc tagaaatagc a                        41

SEQ ID NO: 21            moltype = DNA   length = 33
```

```
FEATURE                 Location/Qualifiers
source                  1..33
                        mol_type = unassigned DNA
                        organism = unidentified
SEQUENCE: 21
nnnnnnnnnn nngttttaga gctagaaata gca                                    33

SEQ ID NO: 22           moltype = DNA  length = 32
FEATURE                 Location/Qualifiers
source                  1..32
                        mol_type = unassigned DNA
                        organism = unidentified
SEQUENCE: 22
nnnnnnnnnn ngttttagag ctagaaatag ca                                     32

SEQ ID NO: 23           moltype = DNA  length = 31
FEATURE                 Location/Qualifiers
source                  1..31
                        mol_type = unassigned DNA
                        organism = unidentified
SEQUENCE: 23
nnnnnnnnnn gttttagagc tagaaatagc a                                      31

SEQ ID NO: 24           moltype = DNA  length = 30
FEATURE                 Location/Qualifiers
source                  1..30
                        mol_type = unassigned DNA
                        organism = unidentified
SEQUENCE: 24
nnnnnnnnng ttttagagct agaaatagca                                        30

SEQ ID NO: 25           moltype = DNA  length = 29
FEATURE                 Location/Qualifiers
source                  1..29
                        mol_type = unassigned DNA
                        organism = unidentified
SEQUENCE: 25
nnnnnnnngt tttagagcta gaaatagca                                         29

SEQ ID NO: 26           moltype = DNA  length = 22
FEATURE                 Location/Qualifiers
source                  1..22
                        mol_type = unassigned DNA
                        organism = unidentified
SEQUENCE: 26
actagtatta tacctaggac tg                                                22

SEQ ID NO: 27           moltype = DNA  length = 27
FEATURE                 Location/Qualifiers
source                  1..27
                        mol_type = unassigned DNA
                        organism = unidentified
SEQUENCE: 27
cgtggcgatg cgcaactggg ctgggac                                           27

SEQ ID NO: 28           moltype = DNA  length = 42
FEATURE                 Location/Qualifiers
source                  1..42
                        mol_type = unassigned DNA
                        organism = unidentified
SEQUENCE: 28
aaggaacgat cgatatgacg aattattctg acatttgcat ag                          42

SEQ ID NO: 29           moltype = DNA  length = 41
FEATURE                 Location/Qualifiers
source                  1..41
                        mol_type = unassigned DNA
                        organism = unidentified
SEQUENCE: 29
cagaataatt cgtcatatcg atcgttcctt aaaaaaatgc c                           41

SEQ ID NO: 30           moltype = DNA  length = 41
FEATURE                 Location/Qualifiers
source                  1..41
                        mol_type = unassigned DNA
                        organism = unidentified
SEQUENCE: 30
cgccatggct tacgacattc cggggatccg tcgacctgca g                           41
```

-continued

```
SEQ ID NO: 31            moltype = DNA   length = 41
FEATURE                  Location/Qualifiers
source                   1..41
                         mol_type = unassigned DNA
                         organism = unidentified
SEQUENCE: 31
ggatccccgg aatgtcgtaa gccatggcgg ccgttacgat c                      41

SEQ ID NO: 32            moltype = DNA   length = 28
FEATURE                  Location/Qualifiers
source                   1..28
                         mol_type = unassigned DNA
                         organism = unidentified
SEQUENCE: 32
cagtgtttcg cgagcgcgaa caagagaa                                     28

SEQ ID NO: 33            moltype = DNA   length = 41
FEATURE                  Location/Qualifiers
source                   1..41
                         mol_type = unassigned DNA
                         organism = unidentified
SEQUENCE: 33
ggagacgcaa tccatcggga tccgtatacc gtgtaggctg g                      41

SEQ ID NO: 34            moltype = DNA   length = 41
FEATURE                  Location/Qualifiers
source                   1..41
                         mol_type = unassigned DNA
                         organism = unidentified
SEQUENCE: 34
gtatacggat cccgatggat tgcgtctccc ggccctcgcc c                      41

SEQ ID NO: 35            moltype = DNA   length = 28
FEATURE                  Location/Qualifiers
source                   1..28
                         mol_type = unassigned DNA
                         organism = unidentified
SEQUENCE: 35
ccgtgtcgga acagcatcca acccatgc                                     28

SEQ ID NO: 36            moltype = DNA   length = 41
FEATURE                  Location/Qualifiers
source                   1..41
                         mol_type = unassigned DNA
                         organism = unidentified
SEQUENCE: 36
tggaagggta aattaaattc cggggatccg tcgacctgca g                      41

SEQ ID NO: 37            moltype = DNA   length = 41
FEATURE                  Location/Qualifiers
source                   1..41
                         mol_type = unassigned DNA
                         organism = unidentified
SEQUENCE: 37
ggatccccgg aatttaattt acccttccaa gtttgtacca a                      41

SEQ ID NO: 38            moltype = DNA   length = 28
FEATURE                  Location/Qualifiers
source                   1..28
                         mol_type = unassigned DNA
                         organism = unidentified
SEQUENCE: 38
ccaactacga aacgctgagc aacccgaa                                     28

SEQ ID NO: 39            moltype = DNA   length = 41
FEATURE                  Location/Qualifiers
source                   1..41
                         mol_type = unassigned DNA
                         organism = unidentified
SEQUENCE: 39
catttcatcc cgctagggga tccgtatacc gtgtaggctg g                      41

SEQ ID NO: 40            moltype = DNA   length = 41
FEATURE                  Location/Qualifiers
source                   1..41
                         mol_type = unassigned DNA
                         organism = unidentified
SEQUENCE: 40
gtatacggat cccctagcgg gatgaaatgg cgcttctttc c                      41
```

-continued

```
SEQ ID NO: 41              moltype = DNA   length = 41
FEATURE                    Location/Qualifiers
source                     1..41
                           mol_type = unassigned DNA
                           organism = unidentified
SEQUENCE: 41
gcagctccag cctacaacgt tatcccctgc ctgaccgggt g                      41

SEQ ID NO: 42              moltype = DNA   length = 41
FEATURE                    Location/Qualifiers
source                     1..41
                           mol_type = unassigned DNA
                           organism = unidentified
SEQUENCE: 42
ggcaggggat aacgttgtag gctggagctg cttcgaagtt c                      41

SEQ ID NO: 43              moltype = DNA   length = 26
FEATURE                    Location/Qualifiers
source                     1..26
                           mol_type = unassigned DNA
                           organism = unidentified
SEQUENCE: 43
ccagataaac cagcgccccg acaaca                                       26

SEQ ID NO: 44              moltype = DNA   length = 84
FEATURE                    Location/Qualifiers
source                     1..84
                           mol_type = unassigned DNA
                           organism = unidentified
SEQUENCE: 44
actgagatat atagatgtga attatccccc acccggtcag gcaggggata acgtggaatt  60
cgtataccgg ggatcggtcg acgt                                         84

SEQ ID NO: 45              moltype = DNA   length = 26
FEATURE                    Location/Qualifiers
source                     1..26
                           mol_type = unassigned DNA
                           organism = unidentified
SEQUENCE: 45
gttgctcatg ccgagcgaaa caaacg                                       26

SEQ ID NO: 46              moltype = DNA   length = 26
FEATURE                    Location/Qualifiers
source                     1..26
                           mol_type = unassigned DNA
                           organism = unidentified
SEQUENCE: 46
cagagataac ttgaagcggg tcaaag                                       26

SEQ ID NO: 47              moltype = DNA   length = 27
FEATURE                    Location/Qualifiers
source                     1..27
                           mol_type = unassigned DNA
                           organism = unidentified
SEQUENCE: 47
cagcgtataa tgcgcgccaa ttgactc                                      27

SEQ ID NO: 48              moltype = DNA   length = 26
FEATURE                    Location/Qualifiers
source                     1..26
                           mol_type = unassigned DNA
                           organism = unidentified
SEQUENCE: 48
aataaagggc gcttagatgc cctgta                                       26

SEQ ID NO: 49              moltype = DNA   length = 26
FEATURE                    Location/Qualifiers
source                     1..26
                           mol_type = unassigned DNA
                           organism = unidentified
SEQUENCE: 49
ctggcgctgc aaattggtgt gaaacc                                       26

SEQ ID NO: 50              moltype = DNA   length = 26
FEATURE                    Location/Qualifiers
source                     1..26
                           mol_type = unassigned DNA
                           organism = unidentified
```

-continued

```
SEQUENCE: 50
gcttcgcttc attgttacca ctcctg                                                   26

SEQ ID NO: 51          moltype = DNA  length = 26
FEATURE                Location/Qualifiers
source                 1..26
                       mol_type = unassigned DNA
                       organism = unidentified
SEQUENCE: 51
gacgatgaca aacctcgcct cgggga                                                   26

SEQ ID NO: 52          moltype = DNA  length = 27
FEATURE                Location/Qualifiers
source                 1..27
                       mol_type = unassigned DNA
                       organism = unidentified
SEQUENCE: 52
gagcagatcg aaaagcaatt acacaaa                                                  27

SEQ ID NO: 53          moltype = DNA  length = 26
FEATURE                Location/Qualifiers
source                 1..26
                       mol_type = unassigned DNA
                       organism = unidentified
SEQUENCE: 53
gttaaacgcg tcggcggttg tggcga                                                   26

SEQ ID NO: 54          moltype = DNA  length = 26
FEATURE                Location/Qualifiers
source                 1..26
                       mol_type = unassigned DNA
                       organism = unidentified
SEQUENCE: 54
ggataacgac ggttgaattc cgccag                                                   26

SEQ ID NO: 55          moltype = DNA  length = 26
FEATURE                Location/Qualifiers
source                 1..26
                       mol_type = unassigned DNA
                       organism = unidentified
SEQUENCE: 55
ctcatcaact catttcattt gttata                                                   26

SEQ ID NO: 56          moltype = DNA  length = 26
FEATURE                Location/Qualifiers
source                 1..26
                       mol_type = unassigned DNA
                       organism = unidentified
SEQUENCE: 56
gaaatacgat ccctccgatc gtgtca                                                   26

SEQ ID NO: 57          moltype = DNA  length = 26
FEATURE                Location/Qualifiers
source                 1..26
                       mol_type = unassigned DNA
                       organism = unidentified
SEQUENCE: 57
ggtgtcatcc actggaacgg cgcgaa                                                   26

SEQ ID NO: 58          moltype = DNA  length = 26
FEATURE                Location/Qualifiers
source                 1..26
                       mol_type = unassigned DNA
                       organism = unidentified
SEQUENCE: 58
cagctggctg atattctgcc gcacgg                                                   26

SEQ ID NO: 59          moltype = DNA  length = 26
FEATURE                Location/Qualifiers
source                 1..26
                       mol_type = unassigned DNA
                       organism = unidentified
SEQUENCE: 59
cggcaatcgc agacctggcg aaactc                                                   26

SEQ ID NO: 60          moltype = DNA  length = 26
FEATURE                Location/Qualifiers
source                 1..26
                       mol_type = unassigned DNA
```

```
                          organism = unidentified
SEQUENCE: 60
gcaaatagct tcctgcctaa cgaagc                                        26

SEQ ID NO: 61            moltype = DNA   length = 26
FEATURE                  Location/Qualifiers
source                   1..26
                         mol_type = unassigned DNA
                         organism = unidentified
SEQUENCE: 61
gatcacattt ccgtaacgtc acgatg                                        26

SEQ ID NO: 62            moltype = DNA   length = 26
FEATURE                  Location/Qualifiers
source                   1..26
                         mol_type = unassigned DNA
                         organism = unidentified
SEQUENCE: 62
gcaagcatta tcggcaacac ctgcct                                        26

SEQ ID NO: 63            moltype = DNA   length = 30
FEATURE                  Location/Qualifiers
source                   1..30
                         mol_type = unassigned DNA
                         organism = unidentified
SEQUENCE: 63
acctgcgtgc aatccatctt gttcaatcat                                    30
```

METHOD FOR SCREENING TARGET GENE USING CRISPRI SYSTEM AND USES THEREOF

CROSS-REFERENCE TO RELATED APPLICATIONS

This application is based on and claims priority from Korean Patent Application No. 10-2021-0188851, filed on Dec. 27, 2021, with the Korean Intellectual Property Office, and claims priority from Korean Patent Application No. 10-2022-0186232, filed on Dec. 27, 2022, with the Korean Intellectual Property Office, the disclosures of which are incorporated herein in their entirety by reference.

INCORPORATION BY REFERENCE OF SEQUENCE LISTING

The content of the electronically submitted sequence listing, file name: Q285792 Substitute Sequence listing as filed.XML; size 57,287 bytes; and date of creation: Mar. 23, 2023, filed herewith, is incorporated herein by reference in its entirety.

TECHNICAL FIELD

The present disclosure relates to a method for screening a target gene using a clustered regularly interspaced short palindromic repeats interference (CRISPRi) system and uses thereof.

BACKGROUND

A CRISPR-Cas9 system consists of single molecular guide RNA (sgRNA) that recognizes a nucleotide sequence of a nucleic acid target and a Cas9 protein, a nuclease that cleaves a double strand of a DNA target. Since the CRISPR-Cas system may specifically bind to the DNA target of any sequence according to a target recognition sequence of sgRNA, the CRISPR-Cas system has been developed as an easy-to-use and useful genome editing technology. Furthermore, deactivated Cas (dCas), of which nucleolytic activity is removed from a Cas protein configuring CRISPR-Cas, has been developed with CRISPR interference (CRISPRi) technology that can act as a potential transcriptional repressor by forming a complex with sgRNA without cleaving the target DNA and may specifically bind to the target DNA sequence, thereby controlling gene expression.

In order to use the CRISPR-Cas system for the purpose of regulating the gene expression, the CRISPRi is a system capable of inducing the gene repression at a target position using dCas from which DNA cleaving enzyme activity of Cas is deficient (removed). The CRISPR is a protein involved in an adaptive immune system in Eubacteria and Archaea, and has been used as a gene editing tool that can easily and quickly create gene insertion and modification at a target site using Cas and sgRNA. At this time, since there is a possibility of causing mutation at a site other than the target site, in order to control the gene expression instead of gene editing for the purpose of solving the problems, CRISPR interference (CRISPRi) was designed as a system capable of inducing the gene repression at a target site using dCas in which the DNA cleaving enzyme activity of Cas is deficient (removed). Through the use of the CRISPRi, since the gene expression at the target site may be repressed without making mutations, the CRISPRi enables gene regulation without genetic modification, and has been used as an efficient tool for DNA sequence-specific regulation of the gene expression in various organisms.

Modulation of the gene expression or deletion of genes in a genome may help to understand the functions of a specific gene in cells. Among many functional genomics tools, transposon mutagenesis has been used as a tool for functional analysis of genes and gene products, but may be biasedly inserted into a specific nucleotide sequence and may not delete essential genes. In addition, it is possible to identify a target for metabolic engineering and obtain a large amount of metabolites using single gene knockout collection, but there is a disadvantage in that it takes a lot of time and money to delete the genes. On the other hand, the CRISPRi may regulate the gene expression without damaging a genome, and has an advantage of being able to reversibly control the expression and repression degrees of essential genes for functional analysis.

Recently, studies have been conducted to identify new target genes, pathways, and mechanisms at a genome level through genotype-phenotype mapping using an sgRNA library using CRISPR screening. Typically, the CRISPR screening is performed in pooled and arrayed formats. First, pooled CRISPR screen introduces a large amount of sgRNA library into cells and identifies target genes by sequencing purified sgRNAs from cells exhibiting specific phenotypic changes. For example, researchers at the University of California used an sgRNA library that targets DNA around transcriptional start sites of 49 genes in human cells to define a DNA window in which gene expression is effectively repressed. The research team of US Regeneron Pharmaceuticals Inc. used CRISPR scissors and a CRISPRa sgRNA library targeting over 20,000 human genes to identify genes and pathways that alter the aggregation process of an abnormal tau protein associated with degenerative brain diseases.

Second, arrayed CRISPR screen introduces sgRNAs targeting one gene per well in a multi-well plate and observes phenotypes that develop in each cell. For example, a recent study showed that an sgRNA library targeting genes selected through omics analysis is used to increase the yield and productivity of fatty acids. An L-proline exporter was successfully discovered in *Corynebacterium glutamicum* using an sgRNA library targeting 397 potential transporter genes.

In most CRISPR screening studies, a plurality of oligonucleotides are individually synthesized using a microarray when constructing an sgRNA library. However, the constructing of the sgRNA library using the synthesized oligonucleotides is expensive and limits the use of the library in a variety of cells. There is a need for a new CRISPR screening study that may overcome these limitations and effectively search for target genes.

SUMMARY

Under the background, the present inventors intensively made researches and efforts to develop a method capable of searching for a target gene that induces changes in phenotypes based on a CRISPR-Cas9 system and a random sgRNA library. When a target recognition sequence (TRS) of the sgRNA is 20 nt, the size of the sgRNA library having all possible nucleotide sequences is $4^{20}$ (to $10^{12}$), which is quite large. Since most of TRSs in an $N_{20}$ sgRNA library is highly likely to be almost absent in sequences of a microbial genome of about $10^6$ in size, the size of the sgRNA library may be reduced by shortening the length of the TRS.

In view of this aspect, the present inventors introduced sgRNAs having TRSs of various lengths into a CRISPR-Cas system expressing dcas9-NG to confirm the minimum length of TRS of the sgRNA required for CRISPRi, and screened a target gene associated with a specific phenotype using a shortened sgRNA random library. As a result, it was confirmed that even when the length of the TRS of sgRNA was shortened to 9 nt, the expression of the target gene may be effectively repressed. To prove this, the present inventors discovered a new target gene that increases its production by applying this to a phenotypic model, identified that the productivity of the target product was increased by manipulating the target gene, and then completed the present disclosure.

Therefore, the present disclosure has been made in an effort to provide a method for constructing a shortened sgRNA random library.

Further, the present disclosure has also been made in an effort to provide a method for screening a target gene based on a clustered regularly interspaced short palindromic repeats interference (CRISPRi) system.

Further, the present disclosure has also been made in an effort to provide a method for selecting cells with increased production of violacein through color analysis of colonies.

Further, the present disclosure has also been made in an effort to provide a method for mass production of a target product of interest.

Other objects and advantages of the present disclosure will be more apparent by the following detailed description and claims.

The terms used herein are used for the purpose of description only, and should not be construed to be limited. The singular expression includes the plural expression unless the context clearly dictates otherwise. In the present disclosure, it should be understood that term "comprising" or "having" indicates that a feature, a number, a step, an operation, a component, a part or the combination thereof described in the specification is present, but does not exclude a possibility of presence or addition of one or more other features, numbers, steps, operations, components, parts or combinations thereof, in advance.

Unless otherwise contrarily defined, all terms used herein including technological or scientific terms have the same meanings as those generally understood by a person with ordinary skill in the art to which example exemplary embodiments pertain. Terms which are defined in a generally used dictionary should be interpreted to have the same meaning as the meaning in the context of the related art, and are not interpreted as ideal or excessively formal meanings unless otherwise defined in the present disclosure.

As used herein, the terms "nucleic acid sequence", "nucleotide sequence" and "polynucleotide sequence" include: oligonucleotide or polynucleotide, and fragments or portions thereof, and DNA or RNA of genomic or synthetic origin, which may be a single-strand or double-strand, and refers to a sense or antisense strand.

Hereinafter, the present disclosure will be described in more detail.

According to one aspect of the present disclosure, the present disclosure provides a method for constructing a shortened sgRNA random library, including the following steps:

(a) synthesizing shortened crRNA that complementarily binds to target DNA, in which the shortened crRNA comprises a shortened target recognition sequence (TRS) consisting of the length selected from the group consisting of 7 to 19 nucleotides from a 5'-terminal; and (b) generating a shortened sgRNA random library including the shortened crRNA by repeating the step of synthesizing the shortened crRNA one or more times.

In this specification, the terms "sgRNA", "single guide RNA" and "guide RNA" are used interchangeably, and refers to a polynucleotide sequence including a guide sequence and any other sequences required for a function of the sgRNA and/or interaction of the sgRNA with one or more Cas proteins to form a CRISPR complex, and the shortened sgRNA comprises crRNA including a shortened target recognition sequence (TRS) and trRNA.

The sgRNA may include a portion (referred to as a spacer region, a target recognition sequence, or a base pairing region) having a sequence complementary to a sequence in the target DNA and a hairpin structure for Cas protein binding. More specifically, the sgRNA may include a portion having a sequence completely or partially complementary to the sequence in the target DNA, a hairpin structure for Cas protein binding, and a terminator sequence. The structure described above may be sequentially present in the order of 5' to 3'. However, the present disclosure is not limited thereto, and any type of guide RNA may be used in the present disclosure as long as the guide RNA includes a main part (target recognition sequence, TRS) of the crRNA or all or part of the complementary part of the target DNA.

In this specification, the TRS, which is a term used while referring to the sgRNA, refers to a nucleotide sequence in a guide RNA that specifies a target site.

When the TRS of the sgRNA is 20 nt, the size of the sgRNA random library having all possible nucleotide sequences is $4^{20}$ (to $10^{12}$), which is an astronomically large unit. In order to synthesize them, since a lot of time, money and efforts are not only required, but also most of TRSs in an $N_{20}$ sgRNA library are highly likely to be almost absent in sequences of a microbial genome of about $10^6$ in size, the $N_{20}$ sgRNA library has 99.999% of unnecessary random sequences. Therefore, the size of the sgRNA library may be reduced by shortening the length of the TRS.

Therefore, in the present disclosure, sgRNAs having TRSs of various lengths were introduced into the CRISPR-Cas system expressing dCas9-NG to confirm the minimum length of the TRS of the sgRNA required for the CRISPRi, and it was found that gene expression may be effectively repressed even when the TRS length of the sgRNA is shortened to a specific length.

Accordingly, the 'shortened TRS' described in the present disclosure generally refers to a target recognition sequence having a length shorter than a 20 nt target recognition sequence complementary to a target sequence having a size of 20 nt, and the length constituting the shortened TRS of the present disclosure is not limited thereto, but is preferably 7 to 19, more preferably 7 to 17, much more preferably 9 to 10, and most preferably 9 from the 5'-terminal.

The sgRNA includes crRNA and tracrRNA, and in the present disclosure, the crRNA may consist of a target recognition sequence or include a target recognition sequence. When the crRNA consists of a shortened target recognition sequence of the present disclosure, the length of the crRNA may be less than 20 nt, preferably 7 to 19, more preferably 7 to 17, much more preferably 9 to 10, and most preferably 9 from the 5'-terminal.

As such, the sgRNA sequence including the short-length TRS also has a shorter length than that of conventional sgRNA including a target recognition sequence of 20 nt. Therefore, in the present disclosure, the sgRNA is referred to as 'shortened sgRNA'.

In the present disclosure, the term "library" means a pool or population including two or more substances of the same kind with different characteristics, a vector library may be prepared using the sgRNA library of the present disclosure, and a cell library may be prepared by introducing the vector into a target cell.

This process may be appropriately performed by those skilled in the art using methods known in the art, as long as the object of the present disclosure may be achieved.

In addition, the shortened sgRNA random library of the present disclosure, according to the purpose of the present disclosure, may be designed to a plurality of shortened sgRNA random libraries including a shortened target recognition sequence (TRS) consisting of 7 to 19 nucleotides. For example, the shortened sgRNA random library may include a plurality of sgRNAs, in which a shortened sgRNA random library including a shortened target recognition sequence consisting of 9 nucleotides complementarily binding to the target DNA and a shortened sgRNA random library including a shortened target recognition sequence consisting of 10 nucleotides complementarily binding to the target DNA are merged.

Accordingly, the shortened sgRNA library of the present disclosure may be a pool including two or more types of sgRNAs having different nucleotide sequences, for example, two or more types of shortened sgRNAs having the same/different target sequences.

In addition, the library of the present disclosure may include a vector library, and the vector library is a vector library into which the shortened sgRNA of the present disclosure is introduced, and may be a pool including two or more vectors having different sequences or components, and for example, two or more vectors having differences in shortened sgRNAs constituting the corresponding vectors as a pool of vectors for each shortened sgRNA of the shortened sgRNA library.

In addition, the library of the present disclosure may include a cell library, and the cell library of the present disclosure may be a pool of two types or more of cells having different characteristics, specifically cells having different shortened sgRNAs included in each cell, for example, different numbers and/or types, particularly, different types of vectors to be introduced, for the purpose of the present disclosure.

Since the object of the present disclosure is to screen a target gene using the shortened sgRNA library, the types of sgRNAs, vectors, and cells constituting each library may be at least two, and the upper limit thereof is not limited as long as the method operates normally.

The complementary binding comprises complete complementary binding or one or more mismatch binding to the target DNA.

The target DNA comprises a nucleotide of a complementary sequence to the target recognition sequence or sgRNA and a protospacer-adjacent motif (PAM). The PAM is a 5'-NG-3' dinucleotide.

Further, according to another aspect of the present disclosure, there is provided a method for screening a target gene based on a clustered regularly interspaced short palindromic repeats interference (CRISPRi) system, the method including the steps of:

(a) introducing a shortened sgRNA random library prepared according to the method of claim 1 into plurality of cells in which a nuclease-deactivated Cas (dCas) protein is overexpressed, thereby generating a plurality of test transformants;

(b) selecting a subject exhibiting a modified phenotype among the transformants, compared to a control group; and (c) confirming a sequence of a shortened TRS of the shortened sgRNA introduced into the selected subject, thereby screening a target gene exhibiting high activity.

The present disclosure may include (d) additionally screening a target gene based on a duplicated gene in a shortened sgRNA random library comprising shortened TRSs having the same length or a duplicated gene between shortened sgRNA random libraries comprising shortened TRSs having the various lengths, among the target genes screened in the step (c).

That is, the target gene of step (c) may be screened based on the duplicated gene in a shortened sgRNA library including shortened TRSs having the same length or the duplicated gene between shortened sgRNA random libraries including shortened TRSs having various lengths and may be appropriately adopted according to the intention and purpose of those skilled in the art.

Subjects (cells) with modified phenotypes are selected according to the method of the present disclosure. The "modification" refers to alteration of the activity, such as regulation, downregulation, upregulation, reduction, repression, increase, decrease, deactivation or activation. Cells with modified gene expression or cellular phenotype may be isolated by using known techniques, such as fluorescence-activated cell sorting (FACS) or magnet-activated cell sorting. The modified phenotype may be recognized through detection of intracellular or cell-surface markers. The intracellular or cell-surface markers may be detected by immunofluorescence staining.

In addition, other applicable modified phenotypic screens include isolation of unique cell populations based on changes in response to stimulation, apoptosis, cell growth, cell proliferation, cell survival, drug resistance, or drug sensitivity.

The modified phenotype may be a change in gene expression or a change in cellular phenotype of at least one target gene. The phenotype is protein expression, RNA expression, protein activity or RNA activity.

The subject exhibiting the modified phenotype is selected for a change in expression of one or more genes compared to the expression level of one or more genes in a control. In some exemplary embodiments, the change in gene expression is an increase or decrease in gene expression compared to the control. The change in gene expression may be determined by changes in protein expression, RNA expression or protein activity.

In the present disclosure, the dCas9 protein may include all variants of dCas9 known in the art as long as the dCas9 protein may achieve the object of the present disclosure.

In the present disclosure, the dCas9 protein is derived without limitation, and non-limiting examples thereof may be derived from a bacterial species selected from the group consisting of *Streptococcus pyogenes, Francisella novicida, Streptococcus thermophilus, Legionella pneumophila, Listeria innocua* and *Streptococcus mutans*, and may be appropriately selected and used by those skilled in the art.

The dCas protein may be a dead CRISPR/Cas enzyme selected from the group consisting of dead Cas9, dead Cas12a, dead Cas12b, and dead Cas12c.

The dCas protein may be dCas9 containing mutations in HNH and RuvC domains.

The dCas9 protein includes at least one mutation selected from the group consisting of D10A, H840A and N863A in *Streptococcus pyogenes* Cas9.

That is, the CRISPRi of the present disclosure represses the expression of a specific gene by using dCas9, a Cas9 protein in which HNH and RuvC domains responsible for nuclease activity are deactivated, and sgRNA complementarily binding to a target DNA sequence. The sgRNA/dCas9 complex binding to a promoter or a coding region of a specific gene may interfere with transcription initiation or elongation by interfering with the binding of a transcription factor or RNA polymerase. The CRISPRi may be used as a platform for various biotechnology researches including genome-scale gene function profiling and microbial metabolic engineering.

The transformation according to the present disclosure includes any method of introducing a target gene (nucleic acid) into an organism, a cell, a tissue or an organ, and may be performed by selecting a suitable standard technique according to a host cell, as known in the art.

These methods include electroporation, protoplast fusion, calcium phosphate ($CaPO_4$) precipitation, calcium chloride ($CaCl_2$)) precipitation, stirring using silicon carbide fibers, agrobacteria-mediated transformation, PEG, dextran sulfate, lipofectamine, thermal shocking, and the like, but are not limited thereto.

According to one exemplary embodiment of the present disclosure, it was confirmed that all of TRSs target a regulatory region or a structural gene of a target gene associated to xylose catabolism.

This means that a method of searching for the target gene using the CRISPRi and the shortened sgRNA random library according to the present disclosure is successful in discovering genes related to phenotypic changes in up to $10^4$ cells by reducing the size of the library.

Therefore, it is demonstrated that genes associated with specific phenotypes may be found by using the shortened sgRNA random library and the CRISPRi of the present disclosure.

Further, according to yet another aspect of the present disclosure, there is provided a method for mass production of a target product of interest, including the following steps:
  (a) deleting two or more target genes obtained according to the target gene screening method described above in a host cell to produce a target product; and
  (b) incubating the host cell to obtain a mass-produced target product of interest.

More specifically, in the present disclosure, a random $N_9$ TRS library of an appropriate size for screening was prepared by confirming the minimum TRS length of sgRNA required for the CRISPRi, and by applying the random $N_9$ TRS library to the CRISPRi, cells with increased production of the target product may be selected through color analysis (phenotype) of the transformed colonies. In addition, in the present disclosure, target genes exhibiting phenotypic changes may be screened by analyzing the redundancy of several candidate genes.

According to one exemplary embodiment of the present disclosure, target genes were screened using the CRISPRi and the shortened sgRNA random library according to the present disclosure, and when a specific target gene among the target genes obtained as the result was single-deleted from a cell and a violacein phenotype was confirmed, it was found that the production of violacein increased remarkably.

The result shows an example of applying the target genes screened using the shortened sgRNA random library and the CRISPRi of the present disclosure, and the scope of the present disclosure may not be interpreted as being limited to the above example.

Therefore, a key technical feature of the present disclosure will be to mass-produce a target product of interest by screening a target gene in a high-throughput manner in a cell and manipulating the screened gene by using a "shortened sgRNA" library having a TRS shorter than 20 nucleotides (nt), which is the length of the TRS of the original sgRNA. To this end, the basic library design method and interpretation of analysis results may be sufficiently expanded by the intentions and purposes of those skilled in the art.

According to the exemplary embodiments of the present disclosure, the method for screening the target gene based on the CRISPRi system can be widely used without a need to create a new sgRNA library based on a genome sequence of an organism, when there is no need for the design and synthesis of a large number of oligonucleotides to construct the sgRNA library, and the sgRNA plasmid is compatible after constructing the CRISPRi system. In addition, it is expected that the present disclosure can be used in wide fields as a tool for genome-scale gene function profiling and studying organisms poorly developed in genetic technology, including pathogens or industrially useful strains or cell lines, and as a platform for electronic regulatory network engineering of genes.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIGS. 4A and 4B show results of comparing phenotypes and violacein production amounts of strains deleted with 17 target genes screened through CRISPRi screening and a wild-type strain.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, Examples are to describe the present disclosure in more detail, and it will be apparent to those skilled in the art that the scope of the present disclosure is not limited by these Examples in accordance with the gist of the present disclosure.

Example 1. Confirmation of Length of Target Recognition Sequence (TRS) in sgRNA Required for CRISPR Interference The present inventors used an *E. coli* HK1160 strain, in which the gene expression of a dCas9-NG protein was inducible by the addition of L-arabinose. The dCas9-NG protein was a protein having 5'-NG as a PAM sequence. The *E. coli* was streaked on an LB solid medium, and then grown colonies were inoculated into 50 ml of a LB liquid medium and incubated at 37° C. until $OD_{600\ nm}$ became 0.4, centrifuged at 3500 rpm for 20 minutes and then washed twice with 40 ml of 10% glycerol to prepare electro-competent cells. Various lengths of sgRNAs recognizing a −10 region of PxylA, a promoter of a xylA gene, as a target sequence were prepared to confirm the length of the target recognition sequence of the sgRNA required for CRISPRi.

Figure 1A:
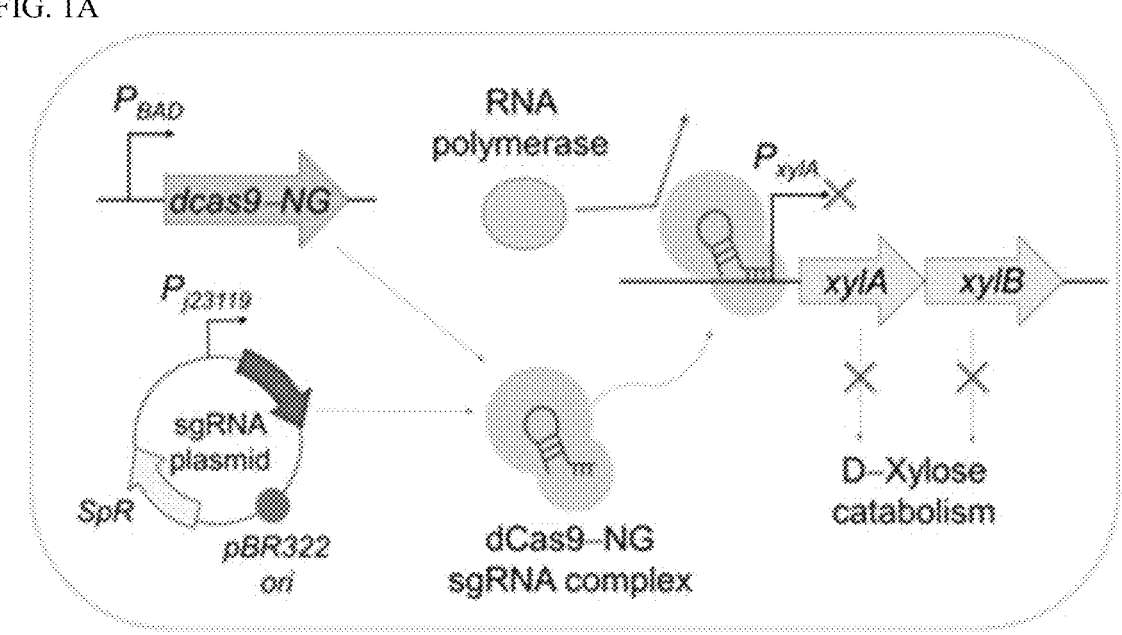
FIG. 1A shows a CRISPRi system that represses the expression of xylA and xylB genes involved in D-xylose metabolism by binding to a xylA promoter of a dCas9-NG/sgRNA complex prepared from a dcas9-NG gene induced by L-arabinose and sgRNA targeting the xylA promoter.
Figure 1B:
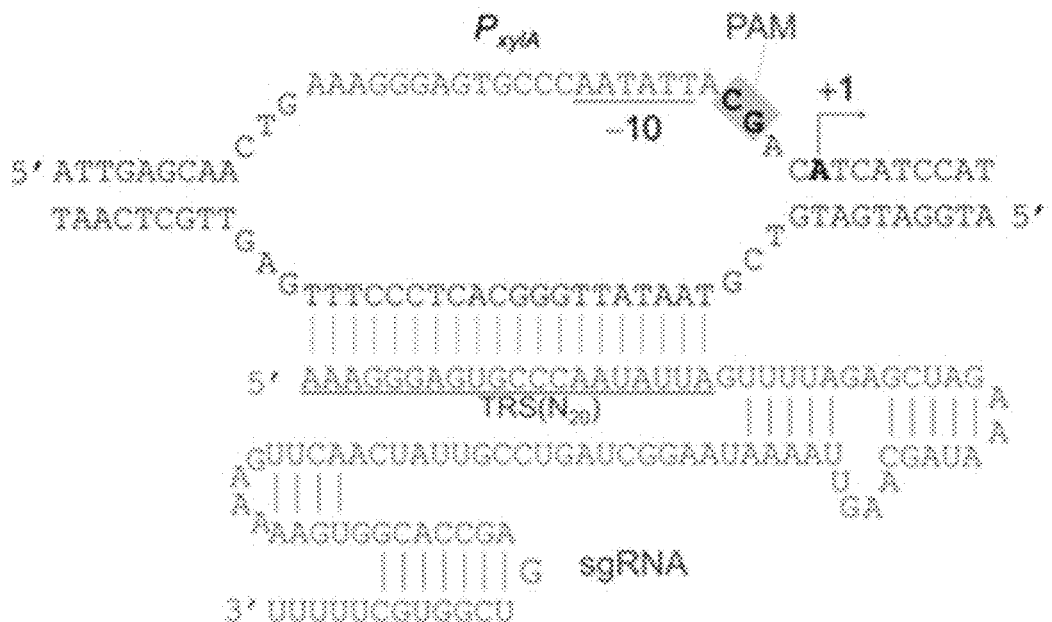
FIG. 1B shows sgRNA with a 20-nucleotide-long TRS targeting a –10 region of the xylA promoter.

Various sgRNA expression plasmids with different lengths of TRS (5'-shortened; $N_7$, $N_8$, $N_9$, $N_{10}$, $N_{11}$, $N_{14}$, $N_{17}$, and $N_{20}$) having the promoter of the xylA gene as the target sequence were constructed as follows: Using a primer pair designed according to a length of the target sequence using plasmid pHK459 as a template, two pieces of DNA with overlapping sequences at both ends were amplified by PCR, and then the two pieces of DNA were connected using Gibson assembly Master Mix to prepare various sgRNA plasmids with different lengths of TRS (FIG. 1B). After the sgRNA expression plasmids with target recognition sequences of various lengths were inserted into HK1160 cells by electroporation, the cells were smeared on a MacConkey selective medium supplemented with 0.3% of D-xylose and L-arabinose, respectively, and then incubated at 37° C.

Figure 1C:
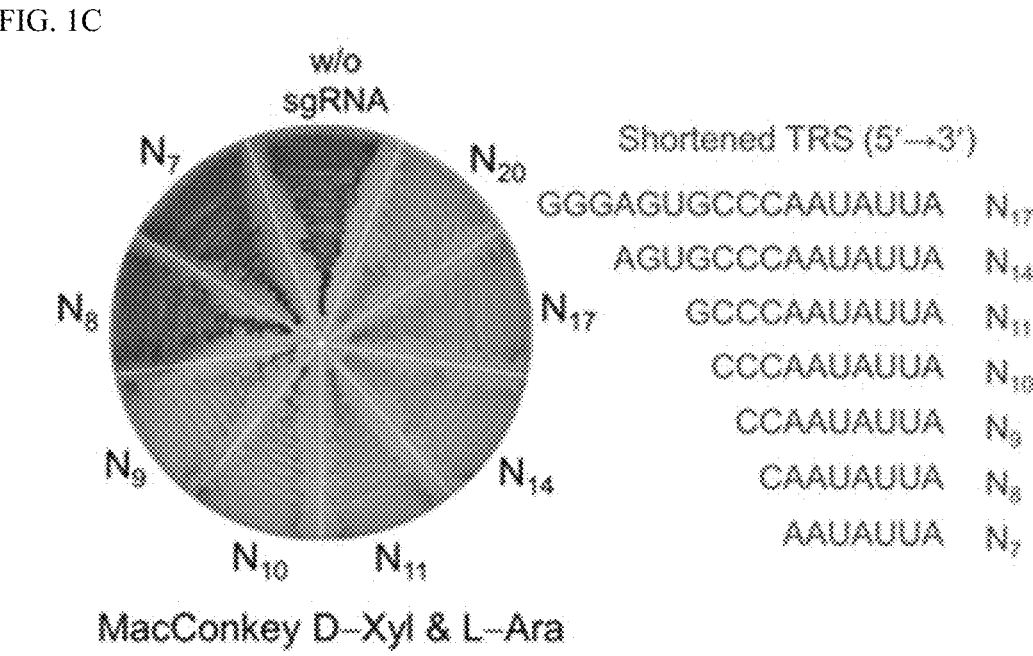
FIGS. 1C and 1D show results of phenotypic changes related to a D-xylose metabolism of a cell and the repression of a xylA gene expression according to various lengths of a TRS in sgRNA, respectively.

When sgRNA plasmids carrying the original length of the TRS ($N_{20}$) and 5'-end-shortened TRS ($N_9$, $N_{10}$, $N_{11}$, $N_{14}$, and $N_{17}$) were transformed, white colonies were observed, indicating the repression of D-xylose metabolic enzyme genes (FIG. 1C). HK1160 cells harboring either sgRNA-deleted or sgRNA plasmids carrying a relatively shorter TRS ($N_7$ and $N_8$) formed red colonies.

Figure 1D:
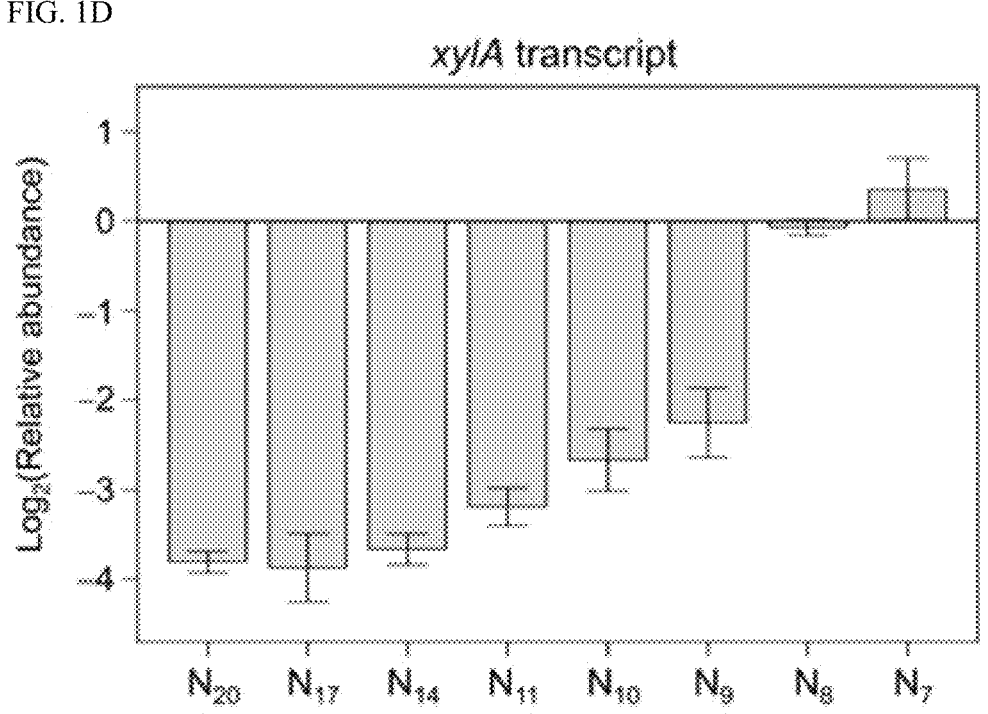

The repression of the xylA promoter by the dCas9-NG/sgRNA complex was verified by quantitative RT-qPCR (FIG. 1D). The relative abundance of xylA transcripts in cells transformed with various sgRNA plasmids was compared to that in cells transformed with the sgRNA-deleted plasmid and determined. The degree of xylA transcriptional repression did not change from $N_{20}$ to $N_{11}$ of the TRS in sgRNAs, but gradually decreased as the length of TRS was shortened from $N_{11}$ to $N_9$. The xylA repression was not observed by CRISPRi in $N_8$ and $N_7$. These results demonstrated that the minimum length of the TRS in sgRNAs required for transcriptional repression and phenotype change was confirmed to be 9 nt.

Primer sequences used in Example above were listed in Table 1.

TABLE 1

| SEQ ID NO: | Primer name | Primer sequence (5'->3') |
|---|---|---|
| 1 | Pxyl-20NG-F | AAAGGGAGTGCCCAATATTAGTTTTAGA GCTAGAAATAGCAAG |
| 2 | Pxyl-20NG-R | TAATATTGGGCACTCCCTTTACTAGTAT TATACCTAGGACTG |
| 3 | Pxyl-17NG-F | AGTGGGAGTGCCCAATATTAGTTTTAGA GCTAGAAATAGCAAG |
| 4 | Pxyl-17NG-R | TAATATTGGGCACTCCCACTAGTATTAT ACCTAGGACTG |
| 5 | Pxyl-14NG-F | ACTAGTAGTGCCCAATATTA GTTTTAGAGCTAGAAATAGCAAG |
| 6 | Pxyl-14NG-R | TAATATTGGGCACT ACTAGTATTATACCTAGGACTG |
| 7 | Pxyl-11NG-F | AATACTAGTGCCCAATATTA GTTTTAGAGCTAGAAATAGCAAG |
| 8 | Pxyl-11NG-R | TAATATTGGGC ACTAGTATTATACCTAGGACTG |
| 9 | Pxyl-10NG-F | TAATACTAGTCCCAATATTAGTTTTAGA GCTAGAAATAGCAAG |
| 10 | Pxyl-10NG-R | TAATATTGGGACTAGTATTATACCTAGG ACTG |
| 11 | Pxyl-9NG-F | ATAATACTAGTCCAATATTAGTTTTAGA GCTAGAAATAGCAAG |
| 12 | Pxyl-9NG-R | TAATATTGGGACTAGTATTATACCTAGGA CTG |
| 13 | Pxyl-8NG-F | TATAATACTAGTCAATATTAGTTTTAGA GCTAGAAATAGCAAG |
| 14 | Pxyl-8NG-R | TAATATTGACTAGTATTATACCTAGGAC TG |
| 15 | Pxyl-7NG-F | GTATAATACTAGTAATATTAGTTTTAGA GCTAGAAATAGCAAG |
| 16 | Pxyl-7NG-R | TAATATTACTAGTATTATACCTAGGACT G |
| 17 | Sm-ATGout | GATACTGGGCCGGCAGGCGCTCCATTGC CC |
| 18 | Sm-TAAout | GCAATGGAGCGCCTGCCGGCCCAGTATC AG |
| 19 | pBR322ori_F | GGGAAACGCCTGGTATCTTTATAGTC |
| 20 | N20_F | NNNNNNNNNNNNNNNNNNNNNGTTTTAG AGCTAGAAATAGCA |
| 21 | N12_F | NNNNNNNNNNNNNGTTTTAGAGCTAGAA ATAGCA |

TABLE 1-continued

| SEQ ID NO: | Primer name | Primer sequence (5'->3') |
|---|---|---|
| 22 | N11_F | NNNNNNNNNNNGTTTTAGAGCTAGAAA TAGCA |
| 23 | N10_F | NNNNNNNNNNGTTTTAGAGCTAGAAAT AGCA |
| 24 | N9_F | NNNNNNNNNGTTTTAGAGCTAGAAATA GCA |
| 25 | N8_F | NNNNNNNN GTTTTAGAGCTAGAAATAGCA |
| 26 | 9NG_R | ACTAGTATTATACCTAGGACTG |
| 27 | xylA_F | CGTGGCGATGCGCAACTGGGCTGGGAC |
| 28 | xylA-vioAF-OF | AAGGAACGATCGATATGACGAATTATTC TGACATTTGCATAG |
| 29 | xylA-vioAF-OR | CAGAATAATTCGTCATATCGATCGTTC CTTAAAAAAATGCC |
| 30 | vioAF-KmR-OF | CGCCATGGCTTACGACATTCCGGGGATC CGTCGACCTGCAG |
| 31 | vioAF-KmR-OR | GGATCCCCGGAATGTCGTAAGCCATGGC GGCCGTTACGATC |
| 32 | vioAB_F | CAGTGTTTCGCGAGCGCGAACAAGAGAA |
| 33 | vioB-CmR-OF | GGAGACGCAATCCATCGGGATCCGTATA CCGTGTAGGCTGG |
| 34 | vioB-CmR-OR | GTATACGGATCCCGATGGATTGCGTCTC CCGGCCCTCGCCC |
| 35 | vioBC_500up | CCGTGTCGGAACAGCATCCAACCCATGC |
| 36 | vioBC-KmR-OF | TGGAAGGGTAAATTAAATTCCGGGGATC CGTCGACCTGCAG |
| 37 | vioBC-KmR-OR | GGATCCCCGGAATTTAATTTACCCTTC CAAGTTTGTACCAA |
| 38 | VioDE_F | CCAACTACGAAACGCTGAGCAACCCGAA |
| 39 | vioDE-CmR-OF | CATTTCATCCCGCTAGGGGATCCGTATA CCGTGTAGGCTGG |
| 40 | vioDE-CmR-OR | GTATACGGATCCCCTAGCGGGATGAAAT GGCGCTTCTTTCC |
| 41 | KmR-xylB-OF | GCAGCTCCAGCCTACAACGTTATCCCCT GCCTGACCGGGTG |
| 42 | KmR-xylB-OR | GGCAGGGGATAACGTTGTAGGCTGGAGC TGCTTCGAAGTTC |
| 43 | xylB_200dn | CCAGATAAACCAGCGCCCCGACAACA |
| 44 | CmR-xylB_R | ACTGAGATATATAGATGTGAATTATCCC CCACCCGGTCAGGCAGGGGATAACGTGG AATTCGTATACCGGGGATCGGTCGACGT |
| 45 | xylB_500dn | GTTGCTCATGCCGAGCGAAACAAACG |
| 46 | BW25113_pyk A-F | CAGAGATAACTTGAAGCGGGTCAAAG |
| 47 | BW25113_pykF -F | CAGCGTATAATGCGCGCCAATTGACTC |
| 48 | BW25113_ptsG | AATAAAGGGCGCTTAGATGCCCTGTA |
| 49 | BW25113_sdaA -F | CTGGCGCTGCAAATTGGTGTGAAACC |

TABLE 1-continued

| SEQ ID NO: | Primer name | Primer sequence (5'->3') |
|---|---|---|
| 50 | BW25113_tnaA | GCTTCGCTTCATTGTTACCACTCCTG |
| 51 | BW25113_tyrR-F | GACGATGACAAACCTCGCCTCGGGGA |
| 52 | BW25113_cra-F | GAGCAGATCGAAAAGCAATTACACAAA |
| 53 | BW25113_ppsR -F | GTTAAACGCGTCGGCGGTTGTGGCGA |
| 54 | BW25113_sad-F | GGATAACGACGGTTGAATTCCGCCAG |
| 55 | BW25113_sdaC -F | CTCATCAACTCATTTCATTTGTTATA |
| 56 | BW25113_livG-F | GAAATACGATCCCTCCGATCGTGTCA |
| 57 | BW25113_ubil-F | GGTGTCATCCACTGGAACGGCGCGAA |
| 58 | BW25113_purL -F | CAGCTGGCTGATATTCTGCCGCACGG |
| 59 | BW25113_met N-F | CGGCAATCGCAGACCTGGCGAAACTC |
| 60 | galT_half_F | GCAAATAGCTTCCTGCCTAACGAAGC |
| 61 | BW25113_rbsA -F | GATCACATTTCCGTAACGTCACGATG |
| 62 | BW25113_gltD-F | GCAAGCATTATCGGCAACACCTGCCT |
| 63 | KmR-ATGout | ACCTGCGTGCAATCCATCTTGTTCAA TCAT |

Example 2. Method for Constructing sgRNA Libraries with Shortened and Random TRS The present inventors have constructed sgRNA expression plasmids having random sequences $N_8$, $N_9$, $N_{10}$, $N_{11}$, $N_{12}$, and $N_{20}$ as target recognition sequences using site-directed mutagenesis. DNA fragments having random regions of different lengths depending on the length of TRS were amplified by PCR using a plasmid pHK459 as a template and a pair of primers phosphorylated at the 5'-terminal. The two amplified fragments were treated with a DpnI restriction enzyme to remove the template and purified. The two purified fragments were ligated using T4 DNA ligase, transformed into a DH5α competent cell, smeared on an LB solid medium, and incubated at 37° C. To confirm the library quality, 10 colonies were randomly selected from random sgRNA libraries (TRS=$N_8$, $N_9$, $N_{10}$, $N_{11}$, $N_{12}$, and $N_{20}$), and TRS sequences of sgRNAs were confirmed by Sanger sequencing. It was confirmed that all 10 sgRNAs were different TRSs. All transformants formed on the solid medium were harvested and the plasmids were purified to obtain a random sgRNA library.

Example 3. Target Gene Screening Using Shortened sgRNA Random Library

The shortened sgRNA random library of Example 2 was inserted into the HK1160 strain overexpressed with dCas9-

Figure 2A:
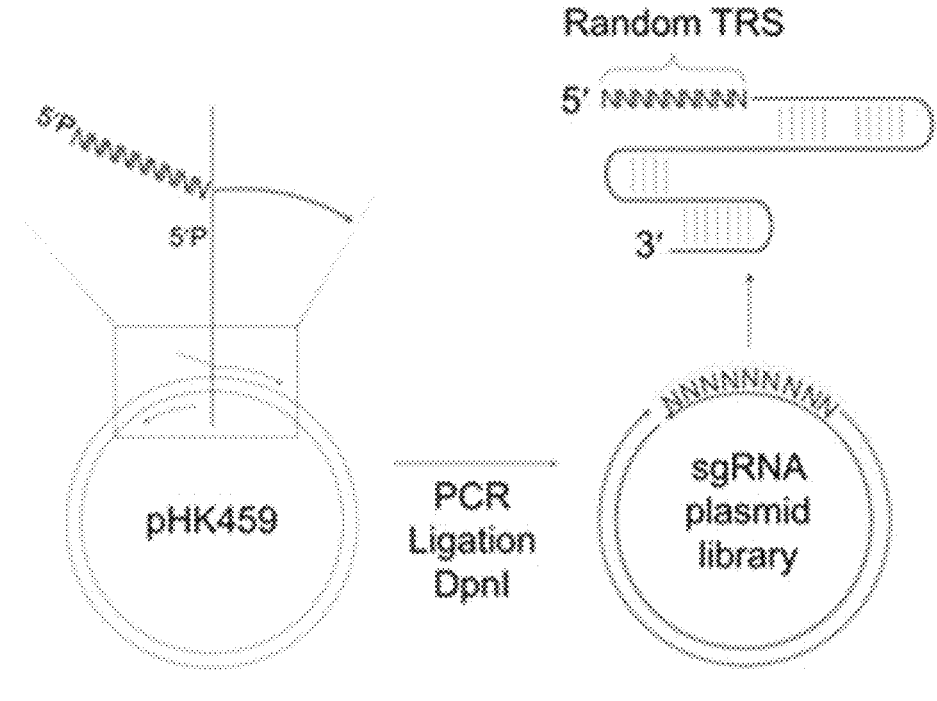
FIG. 2A shows a sgRNA random library constructed using a primer having a random sequence phosphorylated at a 5'-terminal.
Figure 2B:
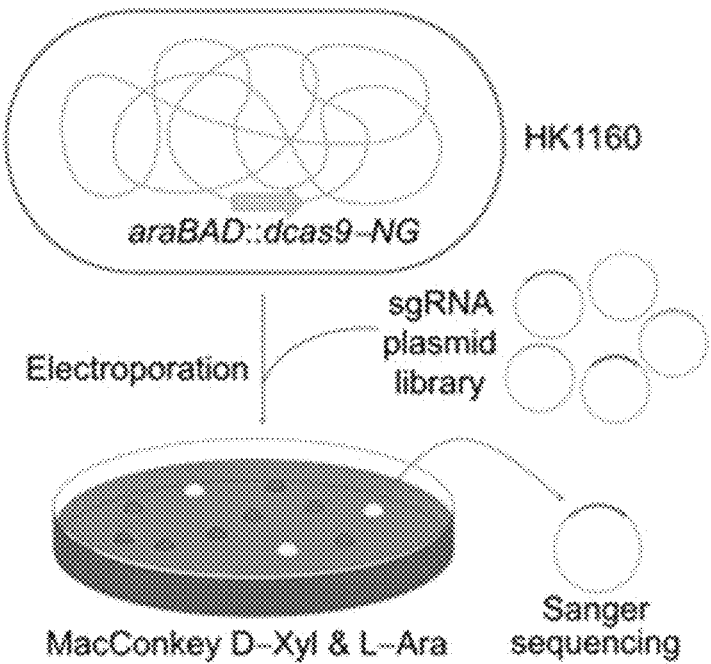
FIG. 2B shows a screening method using the sgRNA random library.
Figure 2C:
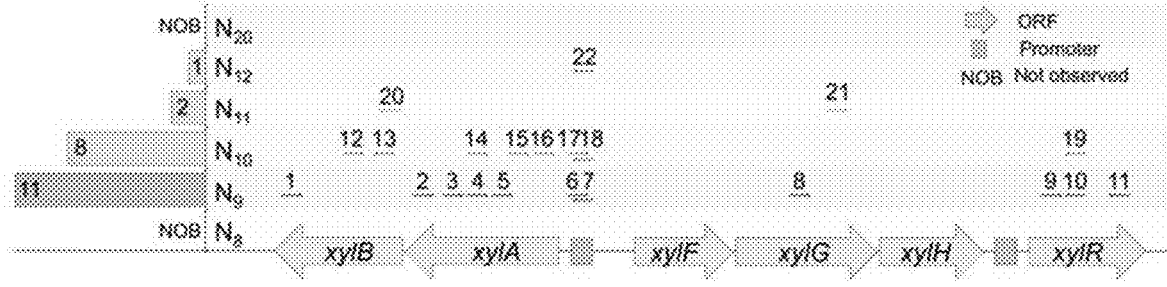
FIG. 2C shows a result of screening target genes associated with a D-xylose metabolism using a sgRNA random library.

NG by electroporation, and then smeared on a MacConkey solid medium supplemented with D-xylose and L-arabinose, and incubated at 37° C. Transformants of about $10^4$ CFU/ligated DNA (µg) were obtained from all the sgRNA random libraries. In the transformed HK1160 cells, 1, 2, 8, and 11 white colonies were observed in the $N_{12}$, $N_{11}$, $N_{10}$, and $N_9$ sgRNA libraries, respectively (FIG. 2C). White colonies were not observed in transformed HK1160 cells in the $N_8$ or $N_{20}$ sgRNA library. For $N_8$, it seems that the expression of the gene may not be repressed because it may not be tightly attached to the target. When the length of the target recognition sequence in sgRNA was 20 nt, the size of random sgRNA with all possible nucleotide sequences was $4^{20}$ (to $10^{12}$). Accordingly, it was unlikely that 20-nt-long TRS sequences in $10^4$ transformed cells will exactly match the genome sequence of the microorganism.

Figure 2D:
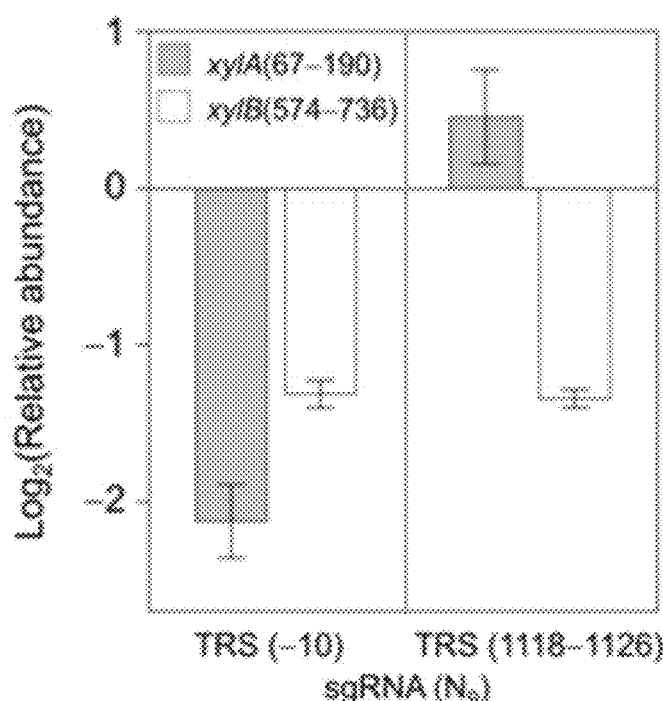
FIGS. 2D and 2E show results of transcriptional repression of xylA and xylB genes according to sgRNA binding sites (promoter and open reading frame).
Figure 2E:
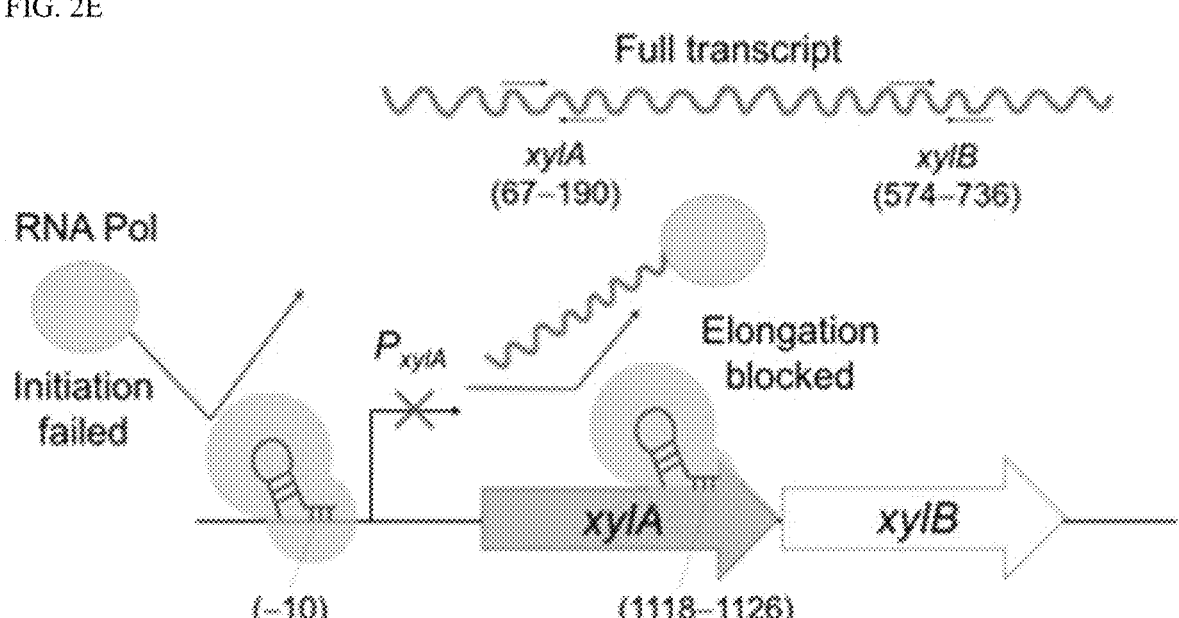

22 different sgRNA plasmids were obtained from 1, 2, 8, and 11 white colonies. Since the target recognition of dCas9-NG was determined by the TRS and the PAM sequence, the TRS and the 5'-NG PAM sequence were confirmed in a D-xylose operon in the *E. coli* genome to identify target nucleotide sequences. As a result, it was confirmed that all 22 types of sgRNA plasmids targeted a regulatory region and a structural gene of genes involved in D-xylose metabolism. Among the 22 types of TRSs, 5 TRSs in the regulatory region and 17 TRSs in the structural gene were identified. Even when the sgRNA was bound to the structural gene using the RT-qPCR, whether the expression of the D-xylose operon gene could be effectively repressed was tested (FIG. 2D). When the sgRNA was bound to the xylA promoter (TRS (−10)), the expression of xylA and xylB was reduced by 2.1- and 1.3-fold, respectively, by CRISPRi. When the sgRNA was bound to the end (1118 to 1126) of the xylA gene, the expression of xylA was not repressed but instead increased by 0.5-fold, and the expression of xylB was decreased by 1.3-fold. When the dCas9-NG/sgRNA was bound to the xylA promoter, the transcripts of xylA and xylB were not formed, so that the repression degree of the gene expression was similarly shown. As a result, it was confirmed that it is possible to find target sequences in the genome of cells with changed phenotypes using a shortened random TRS library.

Example 4. Construction of Recombinant Strain in which Expression of Genes for Violacein Biosynthesis was Induced by D-Xylose The present inventors have prepared an *E. coli* strain (*E. coli* MG1655 xylB::vio ABCDE-CmR) in which a vio-ABCDE operon was inserted into the genome through lambda-red recombination. The *E. coli* MG1655 strain was streaked on an LB solid medium, and then grown colonies were inoculated into 50 ml of a LB liquid medium and incubated at 37° C. until $OD_{600\ nm}$ became 0.4, centrifuged at 3500 rpm for 20 minutes and then washed twice with 40 ml of 10% glycerol to prepare electro-competent cells.

Figure 3A:
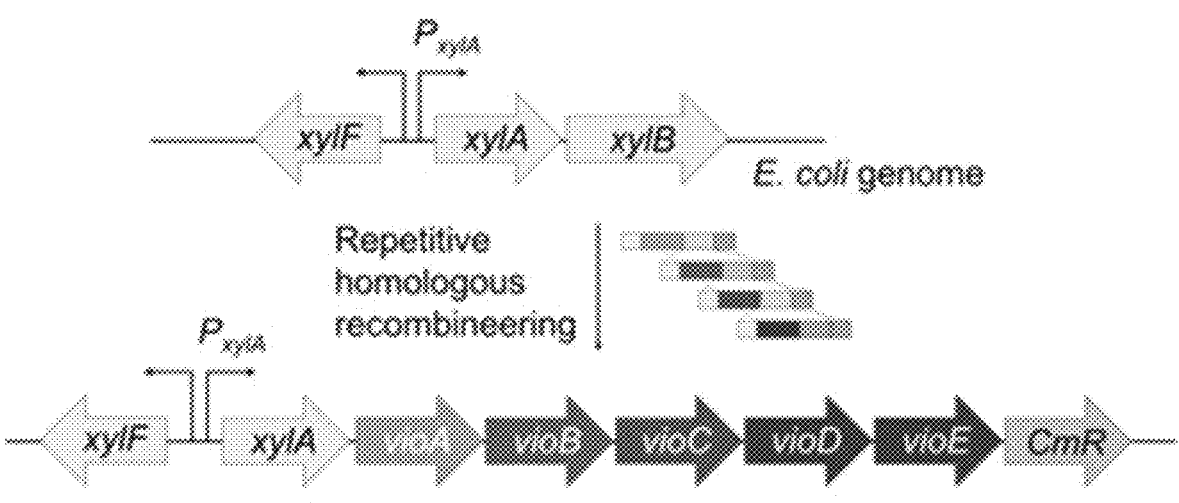
FIG. 3A shows introduction of a violacein biosynthetic gene into an E. coli genome using a homologous recombination method.
Figure 3B:
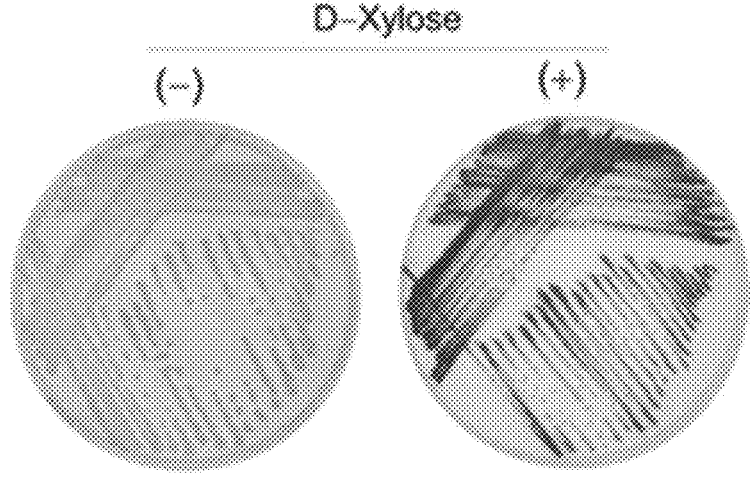
FIG. 3B shows a purple color change of recombinant E. coli colonies by violacein biosynthesis.
Figure 3C:
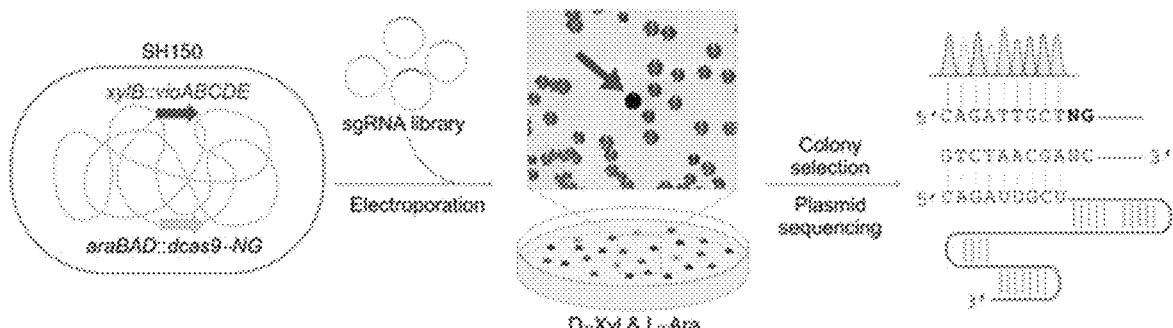
FIG. 3C shows the screening of colonies with increased production of violacein through phenotypic changes of transformed colonies with the sgRNA random library.

The vioABCDE operon was divided and inserted into four DNA fragments vioAF, vioABF, vioBC, and vioDE. Some of the genes for violacein biosynthesis were amplified by PCR from genomic DNA of a *Massilia* sp. NR4-1 strain. A violacein biosynthetic gene part-antibiotic resistance gene cassette was amplified using overlap PCR so as to have a homologous sequence for recombination with a kanamycin or chloramphenicol gene. The amplified PCR product was purified and then inserted sequentially into *E. coli* MG1655 in which a lambda-red recombinant enzyme of a pKD46 plasmid was overexpressed by L-arabinose and located at the back of a promoter in which the gene expression was induced by D-xylose to prepare an SH148 strain. The SH148 strain was streaked on an LB solid medium and an LB solid medium added with D-xylose, and incubated at 30° C. for 24 hours. In the LB solid medium added with D-xylose, the SH148 strain formed purple colonies (FIG. 3B).

P1 transduction was used to construct a violacein-producing *E. coli* strain (*E. coli* MG1655 xylB::vioABCDE-CmR, araBAD::$P_{BAD}$-dcas9-NG-KmR) in which the dcas9-NG gene was inserted into the genome. Single colonies formed by streaking the SH148 strain of Example 4 on the LB solid medium were inoculated into 30 ml of an LB liquid medium added with 10 mM $MgSO_4$ and 5 mM $CaCl_2$, incubated at 37° C. until $OD_{600\ nm}$ became 0.4, and added with P1 vir 300 µl and further incubated for 3 hours until the cells were lysed. Then, the cells were added with 600 µl of chloroform, vortexed, and centrifuged at 3500 rpm for 20 minutes. The cells were completely lysed with chloroform once more to prepare a SH148 P1 lysate.

Single colonies grown by streaking the HK1160 strain having the dcas9-NG gene on the LB solid medium were inoculated into 10 ml of an LB liquid medium added with 10 mM $MgSO_4$ and 5 mM $CaCl_2$ and incubated at 37° C. 1 ml of the culture solution was transferred to a 1.5 ml tube, centrifuged at 12,000 rpm for 5 minutes, and a supernatant was removed. A cell pellet was resuspended in 100 µl of the LB liquid medium added with 10 mM $MgSO_4$ and 5 mM $CaCl_2$, and then added with 10 µl or 100 µl of the SH148 P1 lysate and reacted at 37° C. for 20 minutes. Thereafter, the cell pellet was added with 100 µl of 1 M sodium citrate, and smeared on an LB solid medium added with chloramphenicol and incubated at 37° C. The grown colonies were subjected to PCR to confirm whether the vioABCDE-CmR cassette was inserted at a position of the xylB gene, thereby preparing a SH150 strain.

Example 5. Screening of Target Genes with Increased Violacein Production Using Shortened Random TRS Library The SH150 strain of Example 4 was streaked on the LB solid medium and then the grown single colonies were inoculated in 50 ml of an LB liquid medium and incubated at 37° C. until $OD_{600\ nm}$ became 0.4, and added with L-arabinose at a concentration of 1 mM and further incubated for 3 hours to overexpress a dCas9-NG protein. The SH150 strain was centrifuged at 3500 rpm for 20 minutes, washed twice with 40 ml of 10% glycerol to prepare electrocompetent cells.

Figure 3D:
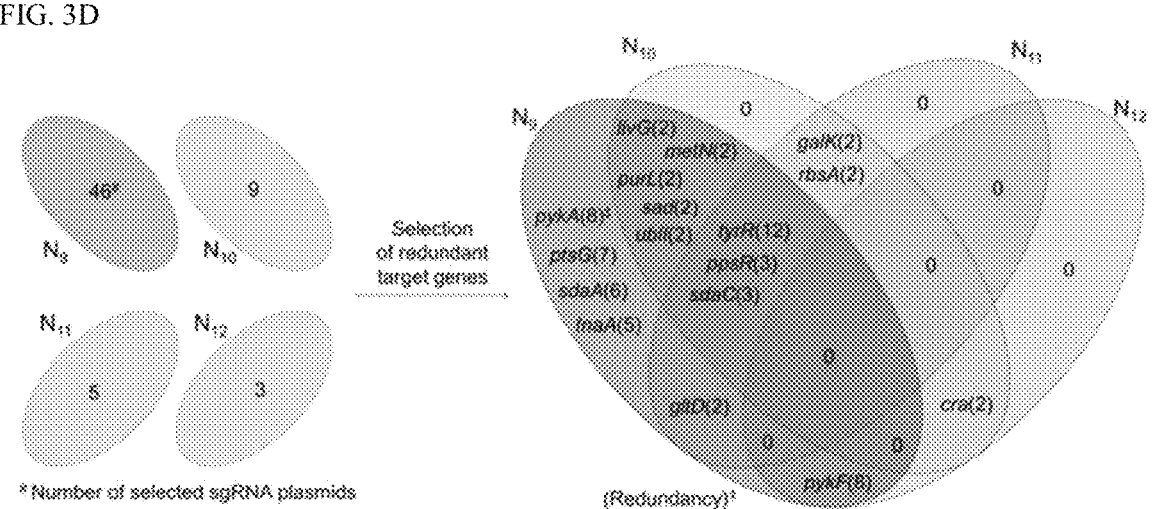
FIG. 3D shows results of screening target genes through redundancy analysis of many candidate genes.

Shortened random sgRNA libraries $N_8$, $N_9$, $N_{10}$, $N_{11}$, $N_{12}$, and $N_{20}$ was inserted into the SH150 strain overexpressed with dCas9-NG by electroporation, and then smeared on the LB solid medium added with 0.3% of D-xylose and L-arabinose and then incubated at 25° C. Among $10^4$ colonies formed on the solid medium, colonies with increased violacein production were screened. Colony colors were extracted from colony images and converted to RGB values. Compared to other colonies, colonies with dark purple color were screened. The sgRNA plasmids were purified from the dark purple colonies and the TRSs of 68 sgRNAs were identified by Sanger sequencing. A total of 63 types ($N_9$=46, $N_{10}$=9, $N_{11}$=5 and $N_{12}$=3) of sgRNA target genes were screened, excluding 5 overlapping TRSs (FIG. 3D).

Since sgRNAs including shortened TRSs may bind to several different sites in the *E. coli* genome, it is difficult to identify which genes cause phenotypic changes among target candidate genes found by CRISPR screening. Accordingly, the present inventors have used a method of analyzing the redundancy of target candidate genes to select target genes. Target genes were screened according to the following criteria: 1) overlapping genes that are repeatedly targeted in the library with same TRS length, and 2) overlapping genes that were repeatedly found in libraries with different TRS length. For the $N_9$ sgRNA library, 460 different sites were identified in the *E. coli* genome by querying 46 TRSs. In particular, 6 genes ptsG, pykA, pykF, sdaA, tnaA, and tyrR were identified five times or more. However, no repeated target genes were found in the $N_{10}$, $N_{11}$, and $N_{12}$ libraries.

Next, overlapping target genes were selected among different sgRNA libraries $N_9$, $N_{10}$, $N_{11}$, and $N_{12}$. Although secA and ligA were found as target genes four and two times, the genes were excluded from the process of screening the target genes for further gene knockout because the genes were known as essential genes in cell growth. Finally, 17 target genes were selected based on the criteria, and each target gene was not biased in the genome (FIG. 3D). In 5 genes cra, ptsG, pykA, pykF, and tnaA, target sequences were identified only in the promoters. In 7 genes galK, gltD, livG, metN, purL, rbsA, and ubil, target sequences were identified only in the middle of the gene. In 5 genes ppsR, sad, sdaA, sdaC, and tyrR, target sequences were identified in both the promoter and the structural region.

Example 6. Construction of Strain with Single-Deleted Target Gene

It was tested whether violacein production was enhanced by repressing the expression of the target gene. The present inventors have used P1 transduction to construct 17 deletion strains in which the target gene was single-deleted. Single colonies formed by streaking kanamycin-resistant strains for 17 target genes in the Keio collection on an LB solid medium were inoculated into 30 ml of an LB liquid medium added with 10 mM $MgSO_4$ and 5 mM $CaCl_2$, incubated at 37° C. until $OD_{600\ nm}$ became 0.4, and added with P1 vir 300 µl and further incubated for 3 hours until the cells were lysed. Then, the cells were added with 600 µl of chloroform, vortexed, and centrifuged at 3500 rpm for 20 minutes. The cells were completely lysed with chloroform once more to prepare a P1 lysate of a kanamycin-resistant strain from the Keio collection.

Single colonies grown by streaking the SH148 strain of Example 4 on the LB solid medium were inoculated into 10 ml of an LB liquid medium added with 10 mM $MgSO_4$ and 5 mM $CaCl_2$ and incubated at 37° C. 1 ml of the culture solution was transferred to a 1.5 ml tube, centrifuged at 12,000 rpm for 5 minutes, and a supernatant was removed. A cell pellet was resuspended in 100 µl of the LB liquid medium added with 10 mM $MgSO_4$ and 5 mM $CaCl_2$, and then 10 µl or 100 µl of the P1 lysate of the 17 kanamycin-resistant strains was added to each SH148 cell and reacted at 37° C. for 20 minutes. Thereafter, the cell pellet was added with 100 µl of 1 M sodium citrate, and smeared on an LB solid medium added with kanamycin and incubated at 37° C.

The grown colonies were subjected to PCR to confirm whether the target gene was deleted in the SH148 strain.

Example 7. Enhancement of Violacein Production by Target Gene Deletion

Figures 4A, 4B:
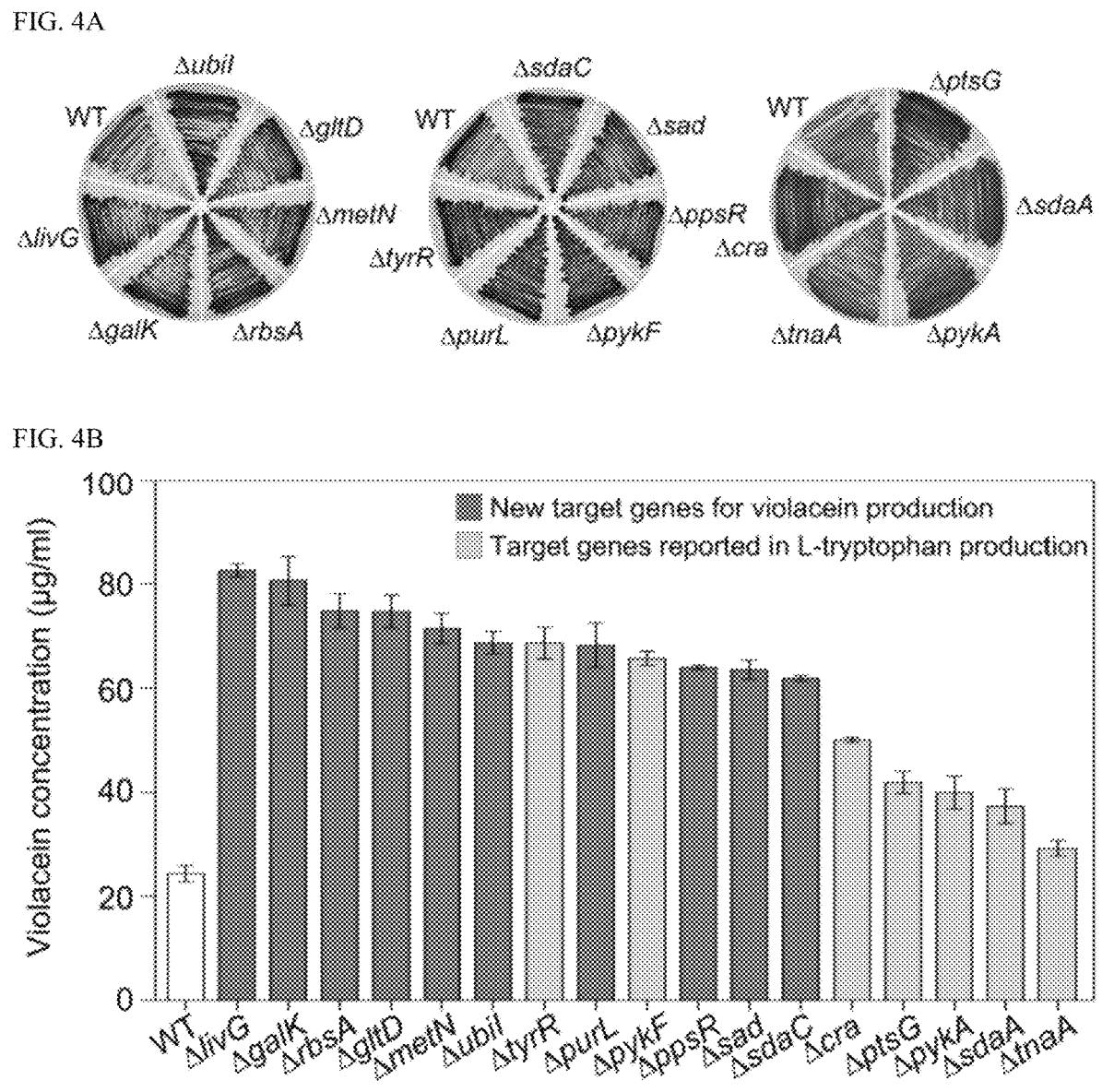

A wild-type strain, SH148, and 17 strains with a single-gene deletion were streaked on a D-xylose-added LB solid medium and incubated at 25° C. Compared to the wild-type strain, all of the 17 deletion strains formed dark purple colonies (FIG. 4A). The wild-type strain and the 17 deletion strains were streaked on the LB solid medium and then the formed single colonies were inoculated into 10 ml of an LB liquid medium and incubated at 37° C. for 12 hours. The culture medium was inoculated into the LB liquid medium added with D-xylose, and then incubated at 25° C. for 48 hours.

For violacein extraction, cells were harvested by centrifugation (4° C., 12,000 rpm, 10 minutes) and the supernatant was discarded. The collected cell pellet was added with methanol (100%, the same volume as the culture medium) and vortexed to be released, and then reacted at room temperature for 20 minutes. Methanol containing violacein was extracted by centrifugation (4° C., 12,000 rpm, 10 minutes). The concentration of violacein in the supernatant was measured by high performance liquid chromatography (HPLC) using a C18 column. As a mobile phase, a mixture of methanol, acetonitrile, and distilled water (1:1:2, v/v) (adjusted to pH 3.6 with acetic acid) was used. Isocratic elution was performed at 30° C. at a flow rate of 0.5 ml/min, and violacein was detected using UV light at 575 nm.

Figure 5:
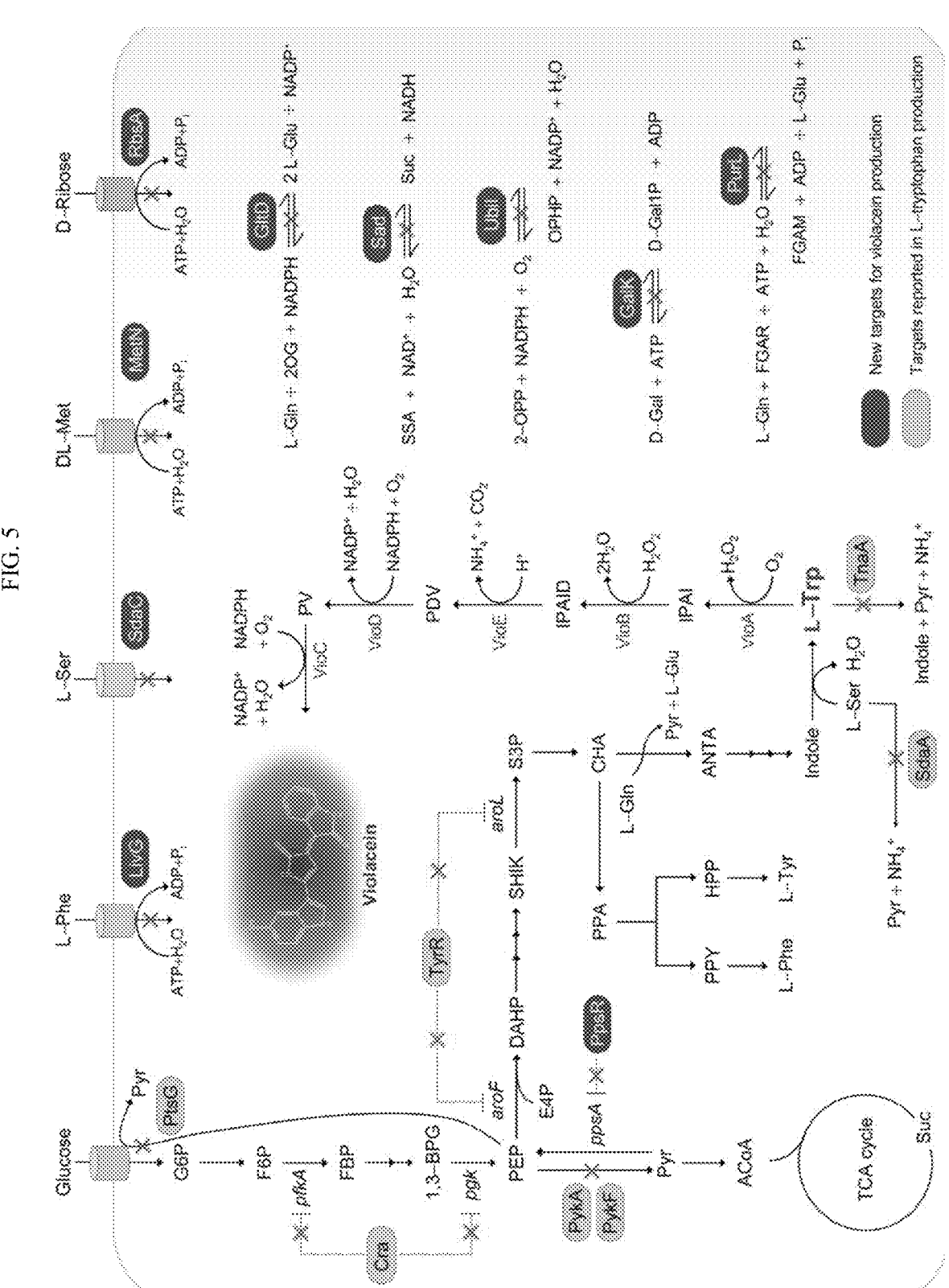
FIG. 5 shows target genes that enhance violacein production found through CRISPRi screening in an intracellular metabolic pathway.

The wild type SH148 strain produced 24.2 µg/ml of violacein, and all the 17 deletion strains showed higher violacein concentrations than the SH148 strain (FIG. 4B). In particular, a single deletion of livG produced 82.6 µg/ml of violacein, 3.4-fold increased compared to the wild-type cell. Among the 17 target genes, 7 genes tyR, pykF, cra, ptsG, pykA, sdaA and tnaA are known to increase the intracellular concentration of tryptophan, a precursor of violacein. Therefore, through CRISPR screening, it was possible to find genes known in tryptophan metabolism engineering in the related art as well as new target genes (FIG. 5), and by deleting the selected target gene, it was possible to prepare strains with enhanced violacein production.

As described above, specific parts of the present disclosure have been described in detail, and it will be apparent to those skilled in the art that these specific techniques are merely preferred exemplary embodiments, and the scope of the present disclosure is not limited thereto. Therefore, the substantial scope of the present disclosure will be defined by the appended claims and their equivalents.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for constructing a shortened sgRNA random library comprising the following steps:

(a) synthesizing shortened crRNA that complementarily binds to target DNA, wherein the shortened crRNA comprises a shortened target recognition sequence (TRS) consisting of the length selected from the group consisting of 7 to 19 nucleotides from a 5'-terminal; and (b) generating a shortened sgRNA random library including the shortened crRNA by repeating the step of synthesizing the shortened crRNA one or more times.

2. The method for constructing the shortened sgRNA random library of claim 1, wherein the shortened TRS consists of 9 nucleotides from the 5'-terminal.

3. The method for constructing the shortened sgRNA random library of claim 1, wherein the complementary binding comprises complete complementary binding or one or more mismatch bindings to the target DNA.

4. The method for constructing the shortened sgRNA random library of claim 3, wherein the target DNA comprises a nucleotide of a complementary sequence to the TRS or sgRNA and a protospacer-adjacent motif (PAM).

5. The method for constructing the shortened sgRNA random library of claim 1, wherein the shortened sgRNA comprises crRNA including a shortened TRS and tracrRNA.

6. A method for screening a target gene based on a clustered regularly interspaced short palindromic repeats interference (CRISPRi) system comprising the steps of:

(a) synthesizing shortened crRNA that complementarily binds to target DNA, wherein the shortened crRNA comprises a shortened target recognition sequence (TRS) consisting of the length selected from the group consisting of 7 to 19 nucleotides from a 5'-terminal;

(b) generating a shortened sgRNA random library including the shortened crRNA by repeating the step of synthesizing the shortened crRNA one or more times;

(c) introducing a the shortened sgRNA random library prepared in the step (b) prepared into plurality of cells in which a nuclease-deactivated Cas (dCas) protein is overexpressed, thereby generating a plurality of test transformants;

(d) selecting a subject exhibiting a modified phenotype among the transformants, compared to a control group; and (e) confirming a sequence of a shortened TRS of the shortened sgRNA introduced into the selected subject, thereby screening a target gene exhibiting high activity.

7. The method for screening the target gene based on the CRISPRi system of claim 6, further comprising:

additionally screening a target gene based on a duplicated gene in a shortened sgRNA random library comprising shortened TRSs having the same length or a duplicated gene between shortened sgRNA random libraries comprising shortened TRSs having the various lengths, among the target genes screened in the step (e).

8. The method for screening the target gene based on the CRISPRi system of claim 6, wherein the dCas protein is a dead CRISPR/Cas enzyme selected from the group consisting of dead Cas9, dead Cas12a, dead Cas12b, and dead Cas12c.

9. The method for screening the target gene based on the CRISPRi system of claim 8, wherein the dCas protein is dCas9 comprising mutations in HlNH and RuvC domains.

10. The method for screening the target gene based on the CRISPRi system of claim 9, wherein the dCas9 protein is derived from a bacterial species selected from the group consisting of *Streptococcus pyogenes, Francisella novicida, Streptococcus thermophilus, Legionella pneumophila, Listeria innocua* and *Streptococcus mutans*.

11. The method for screening the target gene based on the CRISPRi system of claim 10, wherein the dCas9 protein comprises at least one mutation selected from the group consisting of D10A, H840A and N863A in Streptococcus pyogenes Cas9.

12. The method for screening the target gene based on the CRISPRi system of claim 6, wherein the target gene is involved in xylose catabolism.

13. A method for mass-producing a target product of interest comprising the following steps:

(a) synthesizing shortened crRNA that complementarily binds to target DNA, wherein the shortened crRNA comprises a shortened target recognition sequence (TRS) consisting of the length selected from the group consisting of 7 to 19 nucleotides from a 5'-terminal;

(b) generating a shortened sgRNA random library including the shortened crRNA by repeating the step of synthesizing the shortened crRNA one or more times;

(c) introducing the shortened sgRNA random library prepared in the step (b) into plurality of cells in which a nuclease-deactivated Cas (dCas) protein is overexpressed, thereby generating a plurality of test transformants;

(d) selecting a subject exhibiting a modified phenotype among the transformants, compared to a control group;

(e) confirming a sequence of a shortened TRS of the shortened sgRNA introduced into the selected subject, thereby screening a target gene exhibiting high activity;

(f) deleting two or more target genes screened in the step (e) in a host cell to produce a target product of interest; and (g) incubating the host cell to obtain a mass-produced target product of interest.

* * * * *